United States Patent [19]

Yalpani et al.

[11] Patent Number: 5,004,808

[45] Date of Patent: Apr. 2, 1991

[54] AMINOALKYL-DERIVATIVES OF HYDROXYALKYL-CELLULOSES

[75] Inventors: Manssur Yalpani; Magdy M. Abdel-Malik, both of Kirkland, Canada

[73] Assignee: Domtar Inc.

[21] Appl. No.: 216,129

[22] Filed: Jul. 7, 1988

[51] Int. Cl.$^5$ .................. C08B 11/02; C08B 11/145; C08B 11/193; C08B 11/20

[52] U.S. Cl. ........................ 536/56; 536/43; 536/44; 536/56; 536/90; 536/91; 536/96; 536/100

[58] Field of Search ............... 536/43, 44, 56, 90, 536/91, 96, 100, 124

[56] References Cited

PUBLICATIONS

Rowland et al., "The Relative Reactivities of the Hydroxyl Groups of Cotton Cellulose-A Progress Report", Textile Research Journal, vol. 37, No. 12, (Dec. 1967), pp. 1020–1030.

Guthrie et al., "Ion Exchange Celluloses for Chromatographic Separations", Industrial and Engineering Chemistry, vol. 52, p. 935, (Nov. 1960).

Morrison and Boyd, "Reactions of Cellulose", Organic Chemistry, 3rd Edition, pp. 1127–1128 (1978).

*Primary Examiner*—Merrell C. Cashion, Jr.
*Assistant Examiner*—C. Azpuru
*Attorney, Agent, or Firm*—Antoine H. Gauvin

[57] ABSTRACT

A product comprising a water soluble, high molecular weight aminoalkyl-derivative of hydroxyalkyl-cellulose. The molecular weight of said cellulose is at least 50,000 daltons. One of the methods to obtain the product comprises reacting a hydroxyalkyl cellulose in a basic aqueous medium, in the presence of halogenalkylaminohalide compounds, to obtain a hydroxyalkyl cellulose having an alkylamino group which can be used as such or further reacted in the presence of an amide reducing agent, for instance sodium cyanoborohydride and a carbohydrate residue selected from the group consisting of mono-, di-, oligo-saccharides and starch.

32 Claims, No Drawings

AMINOALKYL-DERIVATIVES OF HYDROXYALKYL-CELLULOSES

This invention is directed to a product comprising a water soluble, high molecular weight, aminoalkyl derivative of hydroxyalkyl cellulose having a molecular weight of at least 50,000 daltons and to methods of making and using same. This invention is also directed to new aqueous phase systems obtained from said aminoalkyl derivative of hydroxyalkyl cellulose.

BACKGROUND OF THE INVENTION

Aqueous Two Phase Systems (ATPS) have been employed in several areas of biotechnology, such as in the purification and isolation of biomolecules, cells, and organelles, as well as in bioconversion processes and diagnostic applications. These applications rely on the fact that most biological molecules tend to distribute unevenly between the two liquid phases (where the ratio of the solute concentrations in the upper to lower phases in such phase systems is termed the partition coefficient, ("K").

In cases where the partition coefficient of a particular substrate does not favour efficient separations (i.e., where K is close to unity), the physical parameters of the system may be suitably adjusted to enhance the partitioning by varying parameters such as pH, temperature, polymer nature and concentration, salt, and the like. Of particular interest are the many advantages this technique offers in the large-scale purification of enzymes and proteins in comparison to conventional liquid-solid based separation techniques, such as chromatography. The theoretical and practical aspects of this technique have been described, for example, in Walter, H., Brooks, D. E., and Fisher, D., Partitioning in Aqueous Two-Phase Systems, Academic Press, New York, 1985; Andersson, E., Johansson, A.-C. and Hahn-Barberdal, B., Ann. N. Y. Acad. Sci., 415, 115-118, 1985, Aqueous Two-Phase Systems for Producing Alpha-Amylase Using *Bacillus subtilis;* Larson, M. and Mattiasson, B., Ann. N. Y. Acad. Sci., 415, 144-147, 1985, Continuous Conversion of Starch to Ethanol Using a Combination of an Aqueous Two-Phase System and an Ultrafiltration Unit, Mattiasson, B. and Larson, M., UK Pat. Appl. GB 2,168,617A, 1986). The prior art has employed aqueous solutions of incompatible polymer pairs in the ATPS. Another approach has utilized aqueous polymer/salt systems, e.g., polyethylene glycol/salt, for large scale purifications. However, the presence of high salt concentrations may have undesirable effects (such as denaturation) on many biological substrates, such as proteins and in affinity partitioning, and may therefore not provide a versatile and generally applicable method.

Various incompatible polymer pairs have been reported in the literature, including dextran/polyethylene glycol (PEG), PEG/polyvinyl pyrrolidone (PVP), polypropylene glycol (PPG)/polyvinyl alcohol (PVA), PVA/dextran, PVA/methyl cellulose, PVP/methyl cellulose, PPG/PVP, PPG/dextran, PEG/Ficoll, and other systems based on combinations of derivatives of dextran or starch and synthetic polymers. Much of the prior art has been concerned with the use of dextran/PEG phase systems in view of various practical limitations (e.g., high solution viscosities, long settling times, instability of the polymers, etc.) of many of the above cited polymer combinations. However, a major drawback from a commercial aspect is the high cost of fractionated dextran in these systems, which tends to preclude most large-scale applications.

THE INVENTION

Broadly stated the invention is directed to a product comprising a water soluble, high molecular weight aminoalkyl-derivative of hydroxyalkyl cellulose, said molecular weight being at least 50,000 daltons.

The invention is also directed to a hydroxyalkyl cellulose having an alkylamino group, comprising reacting a hydroxyalkyl cellulose in a basic aqueous medium, in the presence of a compound having an halogen and an amine group to obtain hydroxyalkyl cellulose having an alkylamino group.

The invention is also directed to a method to obtain a hydroxyalkyl cellulose having an alkylaminosaccharide or starch residue, comprising reacting a hydroxyalkyl cellulose having an alkylamino group in a basic aqueous medium, in the presence of a reducing agent and a carbohydrate residue selected from the group consisting of mono-, di-, oligo-saccharides and starch.

In another embodiment, the hydroxyalkyl cellulose is obtained by reacting a cellulose having hydroxy groups with a member selected from the group consisting of epoxy alkyl, and halohydroxyalkyl in an aqueous alkaline medium.

The invention is also directed to water soluble, aminoalkyl derivatives of hydroxyalkyl cellulose forming aqueous multiphase systems with other polymers. Such systems are for instance aqueous solutions of applicant's aminoalkyl-derivative of hydroxyalkyl cellulose forming incompatible pairs with suitable polymers. This may be obtained for instance, with copolymers of polyethylene glycols and polypropyleneglycols available under the trademark "Pluronic" and star copolymers of polypropyleneglycol and polyethyleneoxide available for instance under the trademark "Tetronic 1302 and 908" and having a molecular weight respectively of 7700 and 25,000 daltons, as well as similar systems exhibiting like these two polymer systems useful partitioning properties in the separation of biological substrates, e.g. proteins and cells. One of the advantages of these new aqueous phase systems is that in some cases they require as little as 0.5-1% of the hydroxyalkyl cellulose having alkylamino-saccharide residues for their preparation.

DETAILED DESCRIPTION OF THE PREFERRED EMBODIMENTS

A hydroxyalkyl cellulose may be used directly or if not available may be obtained by reacting in an aqueous alkaline medium, cellulose having hydroxy groups, with a member having a function selected from the group consisting of epoxyalkyl or chloro hydroxyalkyl.

The other ingredients, if any, forming the product may be any substances that do not cause steric hindrance or inhibition action of the aminoalkyl-derivative of hydroxyalkyl cellulose or if desired, the partitioning properties.

By hydroxyalkyl cellulose is meant a cellulose having an aliphatic hydroxy group with or without other functions which are not interfering with the objects of this invention, i.e. not hindering the reactions or partitioning properties. These include, for instance, groups containing-O-alkyl linkages such as alkylether (—O—R), carboxyalkyl (—OR—CH$_2$—COOH), and mixed hydroxyalkyl functions.

Typical examples of hydroxyalkyl celluloses are for instance, hydroxyethyl cellulose, hydroxypropyl cellulose, hydroxy alkylethers such as hydroxyethyl ether and the like.

The hydroxyalkyl cellulose may then be reacted (i.e. an etherification mainly on the hydroxy groups of the side chain containing the hydroxyalkyl groups to replace the hydrogen of the hydroxy groups), with a halo-amino compound, that is a compound having an halogen and an amine group, which may be schematically represented in general by the formula $X-R-NH_2$, both X and $NH_2$ attached to said linking group "R" wherein R is a group linking the halide and amino group, having at least one carbon atoms and X is a halogen selected from the group consisting of fluorine, chlorine and bromine: For instance, the compounds may be halo-alkylamine hydrohalide $XRHN_2$. HX, also sometimes referred to as halogen alkylamine halides or halogenalkylamino hydrohalides, such as bromoalkylamine, hydrobromide, fluoroalkylamin hydrofluoride, etc., chloroalkylamin hydrochloride being most preferred, it forms upon etherification a hydroxyalkyl cellulose having an alkylamino group which may be used as such or reacted under reducing conditions with a carbohydrate residue consisting of a member selected from the group consisting of mono-, di-, oligo-saccharides and starch, in such case the formula being $XRNR_3R_4$. Other examples of the halo-amino compounds having a halogen function and an amine function may be compounds having other links than alkyl and include a compounds having other functional groups "—COO" groups for instance in the form $XR_1CONR_3R_4$ that are not interfering with the halogen and amine groups in accordance with this inventions such as haloalkylamides, for instance 2-Chloroacetamide $ClCH_2CONJ_2$.

The molar ratio of hydroxyalkyl cellulose to basic medium to $X-R-NH_2$ is generally between 2:(2 ±1):(3 ±2) and preferably 1:1:2 between ambient temperature and 100° C. preferably 60–70° C.

Amongst the preferred amide reducing agents are sodium cyanoborohydride ($NaBH_3CN$), sodium borohydride, catalytic reduction and the like.

The choice of the hydroyalkyl aliphatic group with or without other functions as defined above, attached to the cellulose and of the alkyl amino groups produce the necessary characteristics to obtain a suitable partition coefficient "K" in an aqueous medium, yielding new phase systems as will be evidenced from the examples. Amongst the hydroxyalkyl, hydroxyethyl and hydroxypropyl are most preferred, and amongst alkylamino, alkylaminosaccharide, ethylamine and propylamine are preferred.

Amongst the most preferred compositions for making phase systems are those where an amount by weight of 0.5–5% of aminoalkyl-derivative of hydroxyalkyl cellulose is used with 3–15% (preferably 5–10%) of the copolymers of polypropylene glycols and polyethylene glycols. These are generally used at temperatures between 4°–60 C. and preferably ambient temperature. Salts and buffers may be added, if desired.

The following examples will serve to illustrate particular embodiments of the invention.

EXAMPLES

Examples 1 to 10 illustrate some of the ways of making a water soluble, high molecular weight hydroxyalkyl cellulose having alkyl-saccharide residues.

EXAMPLES 1–2

Hydroxypropyl cellulose having a viscosity of 4000–6500 centipoises (cps) (10 parts) was added to water (1000 parts) containing NaOH (10 parts) and stirred mechanically at room temperature for one hour to obtain the sodium salt. 2-Chloroethylamine monohydrochloride (20 parts) was then added and the mixture stirred for 24 hours under the same conditions to displace the sodium ion or the cation. A 500 part fraction of the reaction mixture was withdrawn and dialyzed against water for 4 days then lyophilized to give the aminoethyl derivative of hydroxypropyl cellulose (4 parts), which showed an N-content of 0.24–0.30% (Example 1). The remaining solution was diluted to 1000 parts with water and treated with maltose hydrate (10 parts), followed by sodium cyanoborohydride (2 parts) and stirred under the same conditions for an additional 24 hours. The reaction mixture was dialyzed and lyophilized to give the maltose aminoethyl derivative of hydroxypropyl cellulose (6 parts) with an N-content of 0.91% (Example 2).

EXAMPLES 3–4

Hydroxyethyl cellulose having a viscosity of 4500–6500 cps (10 parts) was added to water (1000 parts) containing NaOH (10 parts) and treated with either 2-Chloroethylamine monohydrochloride (20 parts) or maltose hydrate (10 parts) in the presence of sodium cyanoborohydride (2 parts) as described in Examples 1 and 2 to yield respectively the aminoethyl products having N-contents of 0.16–0.24% (Example 3) and maltose aminoethyl derivatives of hydroxyethyl cellulose, which showed N-contents of 1.05–1.15% (Example 4).

The aminated hydroxyethylcellulose ether obtained in Examples 3 and 4 displayed improved lower surface tension behaviour compared to hydroxyethylcellulose ether in the range of 6–27%, thereby showing good surfactant characteristics.

Typical values of 60.08, 47.48 and 44.78 dynes/cm at 25° C. for hydroxyethylcellulose (Prior Art) as compared against aminated hydroxyethylcellulose (Example 3) and maltose aminoethylcellulose (Example 4) were obtained respectively.

EXAMPLES 5–6

Hydroxypropyl cellulose having a viscosity of 75–150 cps (20 parts) was dissolved in water (700 parts) containing NaOH (20 parts) and the mixture was stirred at room temperature for one hour. 2-Chloroethylamine monohydrochloride was then added (40 parts) and the mixture stirred under the same conditions for 2 hours, and then kept at 60°–70 C. for 72 hours. A sample (350 parts) was then withdrawn, dialyzed and lyophilized to obtain the hydroxypropyl cellulose amine derivative (5.5 parts), which showed an N-content of 0.75% (Example 5). The remaining fraction was treated with maltose hydrate (20 parts) and sodium cyanoborohydride (1.5 parts) at room temperature for 24 hours, to obtain the corresponding amine derivative with an N-content of 2.25% (Example 6).

EXAMPLES 7–8

Hydroxyethyl cellulose having a viscosity of 75–150 cps was treated with 2-Chloroethylamine monohydrochloride as described in Examples 5–6, to yield the aminated derivatives with N-content of 0.97% (Example 7) and of 5.13% with maltose (Example 8).

EXAMPLE 9

Hydroxypropyl cellulose having a viscosity of 4000–6500 cps (10 parts) was reacted with water (300 parts) and NaOH (10 parts) for ½ hour at room temperature. 2-Chloroethylamine mono-hydrochloride (20 parts) was added and stirred under the same conditions for 1 hour, then kept at 60°–70° C. for 72 hours. Maltose hydrate (10 parts) was then added, followed by sodium cyanoborohydride (1.5 parts) and the mixture was mechanically stirred, at room temperature for 24 hours. The mixture was dialyzed for 5 days against water and lyophilized to yield the corresponding amino derivative with an N-content of 2.28%.

EXAMPLE 10

Hydroxyethyl cellulose (10 parts) 4500–6500 cps was dissolved in water (500 parts) containing NaOH (10 parts) and reacted with 2-Chloroethylamine monohydrochloride (20 parts) at 60°–70° C. for 24 hours, then reacted with maltose hydrate (10 parts) and sodium cyanoborohydride (1.5 part) for 24 hours at room temperature to produce the amino derivative with an N-content of 0.62%.

EXAMPLES 11–14

Hydroxypropylcellulose having a viscosity of 4000–6500 cps (20 parts) was reacted with water (2000 parts) and NaOH (20 parts) for one hour at room temperature. 2-Chloroethylamine monohydrochloride (40 parts) was added and stirred under the same conditions for 24 hours.

A sample (500 parts) was then withdrawn, dialyzed and lyophilized to obtain the hydroxypropylcellulose amine derivative (5 parts) which showed a N-content of 0.05–0.19% (Example 11). Another sample (500 parts) was reacted with xylose (10 parts) and sodium cyanoborohydride (1.5 parts) under the same conditions for another 24 hours (total reaction time 48 hours) to obtain the corresponding amine derivative (5 parts) which showed N-content of 0.13–0.29% (Example 12).

A sample (500 parts was withdrawn from the original reaction mixture after 48 hours to obtain the hydroxypropylcellulose amine derivative (4 parts) which showed a N-content of 0.08% (Example 13). Another sample (500 parts was reacted with xylose (10 parts) and sodium cyanoborohydride (1.5 parts) for another 24 hours (total reaction time 72 hours) to obtain the corresponding amine derivative (5 parts) which showed N-content of 0.09–0.15% (Example 14).

EXAMPLES 15–18

Hydroxyethylcellulose having a viscosity of 4500–6500 cps was reacted as described in Examples 11–14 to obtain the hydroxyethylcellulose amine derivative (4 parts) which showed a N-content of 0.1–0.25% (Example 15) and its corresponding xylose derivative (6 parts) which showed N-content of 0.4–0.47% (Example 16) after 24 and 48 hours, respectively. The hydroxyethylcellulose amine derivative (6 parts) which showed N-content of 0.22–0.28% (Example 17) and its xylose derivative (4 parts) with N-content of 0.20–0.38% (Example 18) were also obtained after 48 and 72 hours, respectively.

EXAMPLE 19

Hydroxypropylcellulose having viscosity of 4000–6000 cps was reacted with 2-Chloroacetamide as described in Example 9 to obtain the corresponding amino derivative with N-content of 0.13–0.18%.

EXAMPLE 20

Hydroxyethylcellulose having viscosity of 4500–6000 cps was treated with 2-chloroacetamide as described in Example 10 to obtain the corresponding amino derivative with N-content of 0.10–0.24%.

The following will serve to illustrate products from the above examples which with co-polymers of polypropylene glycol and polyethylene glycol form phase systems that exhibit useful partioning properties in the separation of biological substrates, such as proteins, cellular materials originating from plant, bacterial and mamalian sources, blood etc.

EXAMPLE 21

Using the products as obtained in Examples 3 and 4, the partition behaviour of dog red blood cells was determined. The following results were obtained.

TABLE 1

| Partition behaviour of Dog Red Blood Cells | |
|---|---|
| System | Partition Coefficient |
| Example 3 and "P103" using system A | 0.12 |
| Example 4 and "P103" using system A | 0.15 |
| Example 4 and "P105" using system B | 0.32 |

$^{51}$Cr-labelled, glutaraldehyde cross-linked cells were employed.

System A: 0.83 (w/w) % Example's polymer, 8.35 (w/w) % "P103" or "P105" "Pluronic" polymer, 150 mM sodium chloride, 10 mM sodium phosphate System B: 0.83 (w/w) % Example's polymer, 8.35 (w/w) % "Pluronic P105" polymer, 110 mM sodium phosphate As can be seen from Table 1, cells were preferentially partitioned into the lower phase. This product has good partition behaviour considering that as little as 0.83% aminoalkyl-derivatives of hydroxyalkyl cellulose was used, and that cells normally have a tendency to aggregate at the interphase between the two aqueous polymer phases such as in dextran/PEG systems.

EXAMPLE 22

Using the products obtained from Examples 1 to 8, the partition behaviour of bovine immunoglobulin was determined. The following results were obtained.

TABLE 2

| Partition Behaviour of Bovine IgG | |
|---|---|
| System | Partition Coefficient |
| Example 5 and "P103" | |
| system A | 1.14 |
| system B | 2.06 |
| Example 5 and "P105" | |
| system A | 0.76 |
| system B | 0.77 |
| Example 7 and "P103" | |
| system A | 1.43 |
| system B | 2.38 |
| Example 8 and "P105" | |
| system A | 0.81 |

TABLE 2-continued

Partition Behaviour of Bovine IgG

| System | Partition Coefficient |
|---|---|
| system B | 0.77 |
| Example 1 and "P103" | |
| system D | 0.49 |
| Example 1 and "P104" | |
| system C | 1.14 |
| system D | 2.62 |
| Example 1 and "P105" | |
| system D | 1.63 |
| Example 2 and "P103" | |
| system D | 1.25 |
| Example 2 and "P103" | |
| system C | 0.98 |
| system D | 3.36 |
| Example 2 and "P105" | |
| system C | 0.90 |
| system D | 3.59 |
| Example 3 and "P105" | |
| system C | 0.82 |
| system D | 1.20 |
| Example 4 and "P103" | |
| system C | 1.10 |
| system D | 1.52 |

$^{125}$I-labelled bovin IgG was used.

System A: 3.5 (w/w) % Example's polymer, 10.0 (w/W) % "Pluronic" P103 (having a molecular weight (M.W.) of 4950 daltons) or P105 polymer (M.W. 6500 daltons), 150 mM sodium chloride, 10 mM sodium phosphate.

System B: 3.5 (w/w) % Example's polymer, 10.0 (w/w) % "Pluronic", 110 mM sodium phosphate.

System C: 0.83 (w/w) % Example's polymer, 8.35 (w/w) % "Pluronic", 150 mM sodium chloride, 10 mM sodium phosphate.

System D: 0.83 (w/w) % Example's polymer, 8.35 (w/w) % "Pluronic", 110 mM sodium phosphate.

As is evidenced in Table 2, the polymers disclosed herein display useful partition behaviour in combination with Pluronic polymers. The partitioning of IgG can be effectively achieved into either the upper or lower phases (with high or low partition coefficients, respectively). The performance of these phase systems is also sensitive to the nature of the buffer, as demonstrated in Table 2. The results indicated here compare favourably with those obtained with similar substrates in known phase systems (e.g. dextran/PEG).

Having described the invention, modifications will be evident to those skilled in the art without departing from the spirit of the invention, as defined in the appended claims.

We claim:

1. A product comprising a water soluble, (high molecular weight) (aminoalkyl) aminoalkyl - derivative of hydroxyalkyl cellulose, said aminoalkyl derivative being selected from the group consisting of: amide and amine linked by an alkyl having at least one carbon atom, to the oxygen of the hydroxy group of said hydroxyalkyl cellulose, thereby replacing said hydrogen of the hydroxy group of said hydroxyalkyl, said hydroxyalkyl being a side chain of said cellulose, (said molecular weight being at least 50,000 daltons) said alkyl of said aminoalkyl derivative and said alkyl of said hydroxyalkyl may contain other compatible functional groups and at least one of the hydrogen of said NH$_2$ of said amino being optionally substituted with alkyl and alkyl having other functional groups said other functional groups not hindering the functionality of the amino groups nor the portioning properties of said aminoalkyl derivatives.

2. The product as defined in claim 1 wherein said hydroxyalkyl cellulose is hydroxypropyl cellulose.

3. The product as defined in claim 1 wherein said hydroxyalkyl cellulose is a hydroxyalkyl ether cellulose.

4. The product as defined in claim 1 wherein said hydroxyalkyl cellulose is hydroxyethyl ether cellulose.

5. The product as defined in claim 1 wherein said aminoalkyl derivative is aminoethyl.

6. The product of claim 1 wherein said aminoalkyl-derivative of hydroxyalkyl cellulose has a N-content of 0.6 to 5.1%.

7. A method to obtain an aminoalkyl derivative of (a) hydroxyalkyl cellulose (having an alkylamino group), as defined in claim 1, comprising reacting a hydroxyalkyl cellulose in a basic aqueous medium, to obtain a salt (in the presence of) and then adding a compound having an halogen and an amine group and containing the general formula XRNH$_2$, wherein X is a member selected from the group consisting of fluorine, chlorine and bromine, and R is a linking alkyl group having at least one carbon atom, to displace the cation of said salt and substitute therefor the - RNH$_2$ group thereby to obtain said amino alkyl derivative of hydroxyalkyl cellulose, (having an alkylamino group) said alkyl of said linking alkyl group R and said alkyl of said hydroxyalkyl cellulose optionally containing said other functional groups and at least one of the hydrogen of said NH$_2$ of said amino being optionally substituted with alkyl and alkyl having said other functional groups.

8. The method as defined in claim 7 wherein said compound having a halogen and an amine group is a haloalkyl amine halide compound of the general formula —XRNR$_3$R$_4$, wherein R$_3$ and R$_4$ are each respectively one member of the class consisting of hydrogen, alkyl and alkyl having other compatible functional groups.

9. The method as claimed in claim 7 wherein said compound having a halogen and an amine group is an halogenated amide of the general formula XR$_1$CONR$_3$R$_4$ wherein X is a halogen, and R$_1$ is a link between X and CONR$_3$R$_4$, said link having at least one carbon atom, wherein R$_3$ and R$_4$ are each respectively, one member of the group consisting of hydrogen, alkyl and alkyl having other compatible groups.

10. A method to obtain a hydroxyalkyl cellulose having an aminoalkyl as defined in claim 1, comprising reacting a cellulose having hydroxy groups with a member selected from the group consisting of epoxy alkyl and halohydroxy alkyl, in an aqueous alkaline medium, to obtain a hydroxyalkyl cellulose, reacting said hydroxy alkyl cellulose in a basic medium to obtain a salt and then adding a compound having a halogen and an amine group comprising the general formula XRNR$_3$R$_4$, wherein X is a member selected from the group consisting of fluorine, chlorine and bromine, and R is a linking alkyl group having at least one carbon atom, to displace the cation of said salt and substitute therefor the —RNR$_3$R$_4$ groups thereby to obtain said aminoalkyl derivative of hydroxy cellulose, R$_3$ and R$_4$ being each respectively one member of the class consisting of hydrogen, alkyl and alkyl having other compatible groups, said alkyl of said linking alkyl R and said alkyl of said hydroxyalkyl cellulose optionally containing said other functional groups.

11. The method as defined in claim 7 wherein said hydroxyalkyl cellulose is a member selected from hydroxypropyl cellulose and hydroxyethyl cellulose.

12. The method as defined in claim 7 wherein said hydroxyalkyl cellulose is a hydroxyalkyl ether cellulose.

13. The method as defined in claim 7 wherein said compound having an halogen and an amine group is 2-Chloroacetamide.

14. The method as defined in claim 7 wherein said compound having an halogen and an amine group is 2-Chloroethylamine monochloride.

15. A product as defined in claim 1 being an amino alkyl derivative of cellulose having a molecular weight of at least 50,000 daltons and being selected from the group consisting of aminoethyl derivative of hydroxypropyl cellulose having a N-content of 0.24–0.75%, and aminoethyl derivative of hydroxyethyl cellulose having a N-content of 0.16–97%.

16. The product of claim 1 having improved lower surface tension behavier as compared to hydroxyethyl cellulose.

17. The method as defined in claim 7 wherein the molar ratio of said hydroxyalkyl cellulose to said basic medium to said compound having a halogen and amine group is 2:(2±1):(3±2).

18. The method as defined in claim 17 wherein said molar ratio is 1:1:2.

19. The product as defined in claim 1 wherein said hydroxyalkyl cellulose is a carboxyhydroxyalkyl cellulose.

20. The product as defined in claim 1 being at least one aminoalkyl-derivative of hydroxyalkyl cellulose member selected from the group consisting of: aminoethyl derivative of hydroxypropyl cellulose and aminoethyl derivative of hydroxyethyl cellulose, said member having a molecular weight of at least 50,000 daltons, and being able to form in an aqueous medium a multi-phase system with copolymers of polypropylene glycols and polyethylene glycols.

21. The amino-alkyl derivative of hydroxy alkyl cellulose as defined in claim 1 having a molecular weight of at least 50,000 daltons.

22. The method as defined in claim 7 wherein said hydroxyalkyl cellulose has a molecular weight of at least 50,000 daltons.

23. The method as defined in claim 7 wherein said hydroxyalkyl cellulose is a carboxyhydroxyalkyl cellulose.

24. The product as defined in claim 1 being an amidoalkylamide derivative of hydroxyalkyl cellulose.

25. The product as defined in claim 1 being an amidoacetamide derivative of hydroxyalkyl cellulose.

26. The method of claim 20 which further includes dialyzing and lyophillizing said amino alkyl derivative of hydroxyalkyl cellulose.

27. The product as defined in claim 1, wherein the amino is $NH_2$.

28. The product as defined in claim 1, wherein the amino is $CONH_2$.

29. The method as defined in claim 7, wherein said amino is $NH_2$.

30. The method as defined in claim 7, wherein said amino is $CONH_2$.

31. The method as defined in claim 8 of the general formula $XRNH_2HX$.

32. The method as defined in claim 9 of the general formula $XRICONH_2$.

* * * * *